United States Patent [19]

Markwell et al.

[11] Patent Number: 4,578,393

[45] Date of Patent: Mar. 25, 1986

[54] DIHYDROISOQUINOLINE DERIVATIVES

[75] Inventors: Roger E. Markwell, Great Dunmow; Stephen A. Smith, Bishops Stortford, both of England

[73] Assignee: Beecham Group p.l.c., Middlesex, England

[21] Appl. No.: 663,232

[22] Filed: Oct. 22, 1984

[30] Foreign Application Priority Data

Oct. 20, 1983 [GB] United Kingdom ................ 8328052

[51] Int. Cl.$^4$ .................... A61K 31/47; C07D 217/24; C07D 217/22
[52] U.S. Cl. .................................. 514/310; 514/291; 514/309; 546/90; 546/80; 546/89; 546/79; 546/141; 546/143
[58] Field of Search ................ 546/141, 143; 514/309, 514/310

[56] References Cited

U.S. PATENT DOCUMENTS 4,282,222  8/1981  Bartmann et al. .................. 546/143

FOREIGN PATENT DOCUMENTS 1394702  5/1975  United Kingdom ................ 546/143

OTHER PUBLICATIONS

Chemical Abstracts, vol. 71, Item 38775k (1969), abstracting Csuros et al., "Acta Chim (Budapest)", vol. 60, Nos. 1-2, pp. 177-190.
Chemical Abstracts, vol. 84, Item 179999s (1976), abstracting Deak et al., "Acta Chim Acad Sci Huna", (1976), vol. 88, No. 1, pp. 87-92.
Chemical Abstracts, (plus Chemical Substance Index), vol. 95, Item 115238n, abstracting Kryazeva et al., in "Khim-Farm-Zh", (1981), vol. 15, No. 5, pp. 44-49.

Primary Examiner—Robert T. Bond
Attorney, Agent, or Firm—James F. Haley, Jr.; Paul H. Ginsburg; Irene J. Frangos

[57] ABSTRACT

A compound of formula (I) or a pharmaceutically acceptable salt thereof:

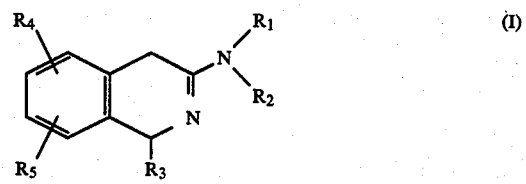

wherein:
  $R_1$ and $R_2$ are independently hydrogen, $C_{1-6}$ alkyl or together are a group X which is $C_{3-6}$ polymethylene optionally interrupted by O, S or $NR_6$ wherein $R_6$ is hydrogen or $C_{1-6}$ alkyl;
  $R_3$ is phenyl, optionally substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl, carboxyl, $C_{1-6}$ alkoxycarbonyl, cyano, $CONR_7R_8$ wherein $R_7$ and $R_8$ are selected from hydrogen or $C_{1-6}$ alkyl or together are a group X; $NR_9R_{10}$ wherein $R_9$ and $R_{10}$ are selected from hydrogen, $C_{1-6}$ alkyl, $C_{2-7}$ alkanoyl or $C_{1-6}$ alkylsulphonyl or together are a group X; $SO_2NR_{11}R_{12}$ wherein $R_{11}$ and $R_{12}$ are selected from hydrogen or $C_{1-6}$ alkyl or together are a group X or $S(O)_mR_{13}$ wherein m is 1 or 2 and $R_{13}$ is $C_{1-6}$ alkyl;
  $R_4$ and $R_5$ are independently selected from hydrogen, $C_{1-6}$ alkyl, cyano, amino, aminocarbonyl or aminocarbamoyl optionally substituted by one or two $C_{1-6}$ alkyl groups or together are a group X, halogen, $CF_3$, nitro, $C_{1-6}$ alkoxy, $C_{1-6}$ alkylthio, $C_{2-7}$ alkanoyloxy, $C_{1-6}$ alkoxy or hydroxy, or together are methylenedioxy or $C_{3-5}$ polymethylene, having anti-inflammatory and/or anti-rheumatic activity, a process for their preparation and their use as pharmaceuticals.

12 Claims, No Drawings

DIHYDROISOQUINOLINE DERIVATIVES

This invention relates to novel compounds having pharmacological activity, to a process for their preparation, to pharmaceutical compositions containing them and to their use in the treatment of mammals.

Khim-Farm Zh. 15(5) 44 (1981) discloses dihydroisoquinoline derivatives of formula (A):

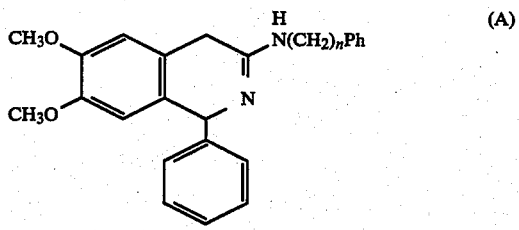

wherein n is 1 or 2. No pharmacological activity has been disclosed for these compounds.

A novel class of compounds which are dihydroisoquinoline derivatives has now been discovered, these compounds having anti-inflammatory and/or anti-rheumatic activity and/or anti-allergy activity.

Accordingly, the present invention provides a compound of formula (I) or a pharmaceutically acceptable salt thereof:

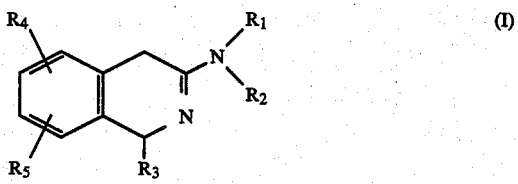

wherein:

$R_1$ and $R_2$ are independently hydrogen, $C_{1-6}$ alkyl or together are a group X which is $C_{3-6}$ polymethylene optionally interrupted by O, S or $NR_6$ wherein $R_6$ is hydrogen or $C_{1-6}$ alkyl;

$R_3$ is phenyl, optionally substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl, carboxyl, $C_{1-6}$ alkoxycarbonyl, cyano, $CONR_7R_8$ wherein $R_7$ and $R_8$ are selected from hydrogen or $C_{1-6}$ alkyl or together are a group X; $NR_9R_{10}$ wherein $R_9$ and $R_{10}$ are selected from hydrogen, $C_{1-6}$ alkyl, $C_{2-7}$ alkanoyl or $C_{1-6}$ alkylsulphonyl or together are a group X; $SO_2NR_{11}R_{12}$ wherein $R_{11}$ and $R_{12}$ are selected from hydrogen or $C_{1-6}$ alkyl or together are a group X or $S(O)_mR_{13}$ wherein m is 1 or 2 and $R_{13}$ is $C_{1-6}$ alkyl;

$R_4$ and $R_5$ are independently selected from hydrogen, $C_{1-6}$ alkyl, cyano, amino, aminocarbonyl, or aminocarbamoyl optionally substituted by one or two $C_{1-6}$ alkyl groups or together are a group X; halogen, $CF_3$, nitro, $C_{1-6}$ alkoxy, $C_{1-6}$ alkylthio, $C_{2-7}$ alkanoyloxy or hydroxy, or together are methylenedioxy or $C_{3-5}$ polymethylene.

Suitable values for $R_1$ and $R_2$ include hydrogen, methyl, ethyl, n- and iso-propyl, n-, sec and tert-butyl, or $R_1$ and $R_2$ together are $X^1$ which is $C_4$ or $C_5$ polymethylene or —$(CH_2)_2$—O—$(CH_2)_2$—. Preferably $R_1$ is hydrogen or methyl and $R_2$ is methyl.

Suitable values for $R_3$ include phenyl and phenyl substituted by one or more of fluoro, chloro, bromo, $CF_3$, nitro, methyl, ethyl, n- and iso-propyl, n-, sec- and tert-butyl, methoxy, ethoxy, n- and iso-propoxy, methylthio, ethylthio, n- and iso-propylthio, acetyl, propionyl, carboxyl, methoxycarbonyl, ethoxycarbonyl, cyano, $CONH_2$, $NR_9{}^1R_{10}{}^1$ wherein $R_9{}^1$ and $R_{10}{}^1$ are selected from hydrogen, methyl, methylsulphonyl or together are a group $X^1$ as defined; $SO_2NR_{11}R_{12}$ wherein $R_{11}{}^1$ and $R_{12}{}^1$ are selected from hydrogen or methyl, methylsulphonyl, ethylsulphonyl, methylsulphinyl or ethylsulphinyl. Favourably $R_3$ is phenyl optionally substituted by one or two of fluoro, chloro, bromo, $CF_3$, nitro, methyl, cyano, methoxy, or methylthio. Preferably $R_3$ is 2-chlorophenyl, 2-bromophenyl, 2-fluorophenyl or 2-chloro-6-fluorophenyl.

Suitable values for $R_4$ and $R_5$ include hydrogen, methyl, ethyl, n- and iso-propyl, cyano, amino, aminocarbonyl or aminocarbamoyl optionally substituted by one or two methyl groups, fluoro, chloro, bromo, nitro, methoxy, hydroxy, acetoxy, n-butyryloxy or 2,2-dimethylpropionyloxy, or together are methylenedioxy. Favourably $R_4$ and $R_5$ are selected from hydrogen, methoxy or hydroxy. Preferably $R_4$ and $R_5$ are both hydrogen or $R_4$ is 6-hydroxy or 6-methoxy and $R_5$ is hydrogen, $R_4$ is hydrogen and $R_5$ is 8-hydroxy or 8-methoxy or $R_4$ and $R_5$ are 6,7-dihydroxy.

There is a group of compounds within formula (I) wherein $R_1$ is as defined in formula (I) and $R_3$ is phenyl optionally substituted by halogen, $CF_3$, nitro, $C_{1-6}$ alkyl, CN, $COR_7R_8$; $NHR_{10}R_{11}$, aminosulphonyl or $C_{2-7}$ alkanoyl; and $R_4$ and $R_5$ are independently selected from hydrogen, halogen, $CF_3$, nitro, $C_{1-6}$ alkoxy or hydroxy, or together are methylenedioxy.

There is a group of compounds within formula (I) of formula (II):

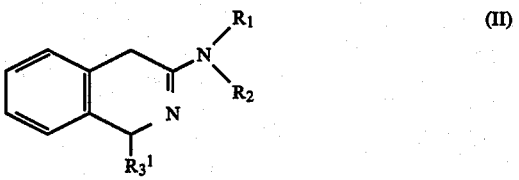

wherein $R_3{}^1$ is phenyl optionally substituted by one or two of halo, nitro, cyano or methyl; and the remaining variables are as defined in formula (I).

Suitable and preferred values for $R_1$, $R_2$ and $R_3{}^1$ are as described for the corresponding variables in formula (I).

There is a further group of compounds within formula (I) of formula (III):

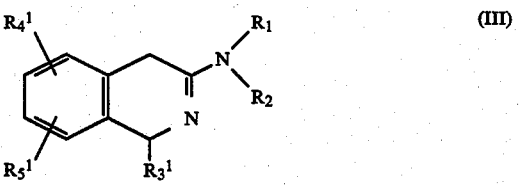

wherein $R_4{}^1$ is hydrogen, halogen, $C_{1-6}$ alkoxy, $C_{2-7}$ alkanoyloxy or hydroxy and $R_5{}^1$ is $C_{1-6}$ alkoxy, $C_{2-7}$ alkanoyloxy or hydroxy; or $R_4{}^1$ and $R_5{}^1$ together are methylenedioxy; and $R_3{}^1$ is as defined in formula (II).

Suitable and preferred values for the variable groups are as described for the corresponding variables under formula (I).

There is a favoured sub-group of compounds within formula (III) of formula (IV):

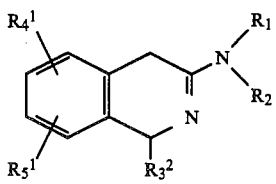

wherein $R_3^2$ is phenyl substituted by one or two of fluoro, chloro or bromo or cyano and the remaining variables are as defined in formula (I).

The compounds of the formula (I) can form acid addition salts with acids, such as the conventional pharmaceutical acids, for example, maleic, hydrochloric, hydrobromic, phosphoric, acetic, fumaric, salicylic, citric, lactic, mandelic, tartaric and methanesulphonic.

The compounds of formula (I) also form solvates such as hydrates, which form an aspect of the invention.

The compounds of formula (I) have at least one asymmetric centre and therefore exist in more than one stereoisomeric form. The invention extends to all such forms and to mixtures thereof, including racemates.

The present invention also provides a process for the preparation of a compound of formula (I), or a pharmaceutically acceptable salt thereof which process comprises the reaction of a compound of formula (V):

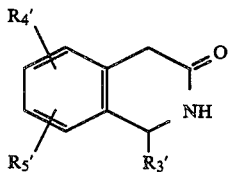

wherein $R_3'$, $R_4'$ and $R_5'$ are $R_3$, $R_4$ and $R_5$ or groups or atoms convertible thereto; with either (i) $R_1'R_2'NCOQ_1$ wherein $Q_1$ is a leaving group or (ii) an alkylating agent followed by treatment with $R_1'R_2'NH$ wherein $R_1'$ and $R_2'$ are $R_1$ and $R_2$ or groups or atoms convertible thereto;

and thereafter optionally converting $R_1'$ and/or $R_2'$ when other than $R_1$ and/or $R_2$ to $R_1$ and/or $R_2$ respectively; converting $R_3'$, $R_4'$ or $R_5'$ to $R_3$, $R_4$ and/or $R_5$ respectively; and/or forming a pharmaceutically acceptable salt thereof.

Suitable values for $Q_1$ include halogen, such as chloro or bromo, preferably chloro.

The reaction (i) of a compound of formula (V) with $R_1'R_2'NCOQ_1$ may either take place in an inert solvent, such as xylene or higher boiling solvent or, more preferably in neat $R_1'R_2'NCOQ_1$ at high temperature 150°–180° C. for example 170°–175° C.

Suitable values for the alkyl group in (ii) include methyl, ethyl, n- and iso-propyl. Preferably the alkyl group is methyl or ethyl. Suitable alkylating agents include dialkylsulphate, alkyl iodide or trialkyloxonium tetrafluoroborate. The reaction is preferably carried out in an inert solvent such as dichloromethane and the alkylating agent is preferably triethyloxonium tetrafluoroborate. The intermediate is of formula (VI) or a salt thereof:

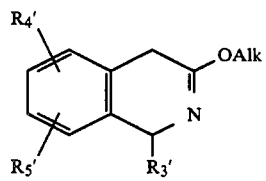

wherein Alk is an alkyl group and the remaining variables are as defined in formula (V). The intermediate of formula (VI) is the tetrafluoroborate salt when the alkylating agent is a trialkyloxonium tetrafluoroborate. $HNR_1'R_2'$ is then added to the compound of formula (VI), without isolation and the compound of formula (I) extracted by conventional methods.

$R_1'$ and $R_2'$ may be converted to $R_1/R_2$ alkyl groups by conventional amine alkylation, dealkylation or deacylation. When $R_1'$ or $R_2'$ is benzyl or substituted benzyl it may be converted to an $R_1$ or $R_2$ hydrogen atom by catalytic hydrogenation or other method of reduction. Conversions of an aromatic group $R_3'$ or group or atom $R_4'$ or $R_5'$ into $R_3$, $R_4$ or $R_5$ are generally known in the art of aromatic chemistry. For example, a nitro group may be converted to an amino group by conventional catalytic hydrogenation. $R_1'$ and $R_2'$ are preferably $R_1$ and $R_2$ respectively.

The compounds of formula (I) may be converted into their pharmaceutically acceptable acid addition salts by reaction with the appropriate organic or mineral acids.

Compounds of formula (V) may be prepared by the method described in Acta Chimica Academide Scientiarum Hungaricae 1969, 60(1-2), 177 that is by reaction of a compound of formula (VII):

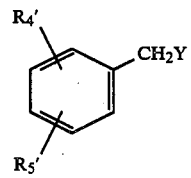

where Y is CN or $CONH_2$ with an aldehyde of formula (VIII):

$$R_3'CHO \qquad (VIII)$$

in polyphosphoric acid at a temperature of 100° to 140° C. The reaction is preferably carried out in polyphosphoric acid containing 82 to 84% of phosphorus pentoxide and preferably at 100° to 140° C., without using any other solvent. The reaction takes place generally within 1 to 12 hours.

As mentioned previously, the compounds of formula (I) exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form.

Intermediates of formula (V) form an aspect of the invention.

The present invention further provides a pharmaceutical composition, which comprises a compound of formula (I) or a pharmaceutically acceptable salt thereof and a pharmaceutically acceptable carrier.

A composition of this invention is useful in the treatment of rheumatism and arthritis and in the treatment of pain and other inflammatory conditions and also in the treatment of and propylaxis of bronchial asthma, rhinitis, hay fever and allergic eczema.

A composition of the invention, which may be prepared by admixture, may contain a diluent, binder, filler, disintegrant, flavouring agent, colouring agent, lubricant, preservative in conventional manner. These conventional excipients may be employed in conventional manner, for example as in the preparation of compositions of ketoprofen, indomethacin, naproxen, acetylsalicyclic acid and other analgesic or anti-inflammatory agents.

A composition of the invention may be adapted for oral, topical, rectal or parenteral—intravenous or intramuscular—administration but oral administration is preferred.

A compostion of the invention will preferably be in the form of a unit dose, such as a tablet or capsule or a sachet containing reconstitutable powder. A unit dose for inflammatory diseases will generally contain from 20 to 1000 mg and preferably will contain from 30 to 500 mg, in particular 50, 100, 150, 200, 250, 300, 350, 400, 450 or 500 mg. The compostion may be administered once or more times a day, for example 2, 3 or 4 times daily, so that the total daily dose for a 70 kg adult will normally be in the range 100 to 3000 mg. Alternatively the unit dose will contain from 2 to 20 mg of a compound of the invention and be administered in multiples, if desired, to give the preceding daily dose.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For topical administration, the preparations may also be presented as an ointment, cream, lotion, gel, aerosol, or skin paint for topical application.

The present invention additionally provides a method of treating an inflammatory and/or a painful condition such as rheumatism and/or allergic conditions in mammals, such as humans, which comprises administering an effective amount of a compound, pharmaceutically acceptable salt or composition of the invention to the mammal; and also provides a compound, pharmaceutically acceptable salt or composition of the invention for use in the treatment of inflammatory and/or painful conditions, such as rheumatism, and/or allergic conditions in mammals.

The following Descriptions and Examples illustrate the preparation of compounds of the invention and the following biological data illustrates their pharmacological activity.

DESCRIPTION 1

1-(2-Chlorophenyl)-1,4-dihydroisoquinol-3-one

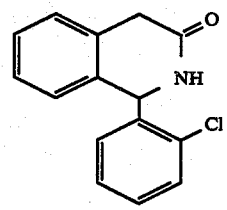

This material was prepared in a similar manner to that described in *Acta Chimica Academiae Scientiarum Hungaricae* 1969, 60(1–2), 177. Thus a mixture of benzyl cyanide (40 g, 342 mmol) and polyphosphoric acid (200 g) was heated and stirred at 80° C. for 45 minutes. 2-Chlorobenzaldehyde (24 g, 171 mmol) was added with very vigorous stirring over 25 minutes. The mixture was heated to 135° C. for 3½ h, cooled to 100° C. and poured into water (450 ml). 0.88 Ammonium hydroxide (600 ml) was added and the mixture left overnight. The precipitate was filtered off and refluxed in 5% sodium hydroxide (500 ml). The mixture was filtered hot after 2 h and the solid (30 g) chromatographed ($SiO_2$, 200 g) using chloroform as eluent. This gave a solid that was crystallised (ethanol) to give 1-(2-chlorophenyl)-1,4-dihyroisoquinol-3-one (20.5 g, 47%) m.p. 180°–2° C.

NMR $CDCl_3$ δ3.68 (2H, m), 6.16 (1H, b), 6.5–7.6 (9H, m).

H.R.M.S. $C_{15}H_{12}NOCl$ requires 257.0607. Found: 257.0609. Analysis $C_{15}H_{12}NOCl$ requires C, 69.91; H, 4.69; N, 5.43; Cl, 13.76. Found: C, 69.54; H, 4.55; N, 5.31; Cl, 13.76%.

The following descriptions (2–15) were prepared in a similar manner to that described in Description 1.

DESCRIPTION 2

1-(2-Bromophenyl)-1,4-dihydroisoquinol-3-one

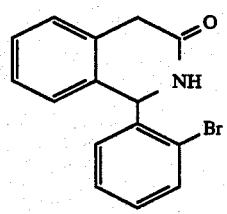

m.p. 193°–197° C. (from ethanol).

Analysis: $C_{15}H_{12}NOBr$ requires C, 59.62; H, 4.00; N, 4.64; Br, 26.44%. Found: C, 59.42; H, 3.91; N, 4.58; Br, 26.65%.

DESCRIPTION 3

1-(2-Trifluoromethylphenyl)-1,4-dihydroisoquinol-3-one

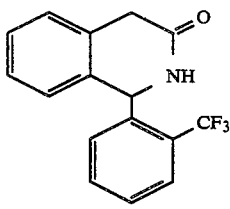

m.p. 210°–212° C. (from ethanol/ethyl acetate).
Analysis: $C_{16}H_{12}N_1O_1F_3$ requires C, 65.98; H, 4.15; N, 4.81%. Found: C, 65.76; H, 4.09; N, 4.79%.

DESCRIPTION 4

1-(2-Chloro-6-fluorophenyl)-1,4-dihydroisoquinolin-3-one

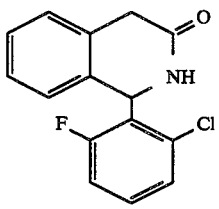

m.p. 249°–252° C. (from dioxan).
Analysis: $C_{15}H_{11}NOClF$ requires C, 65.35; H, 4.02; N, 5.08%. Found: C, 65.13; H, 3.98; N, 5.02%.

DESCRIPTION 5

1-(3-Chlorophenyl)-1,4-dihydroisoquinol-3-one

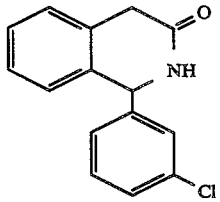

m.p. 133°–134° C. (ethanol).
Analysis: $C_{15}H_{12}NOCl$ requires C, 69.91; H, 4.69; N, 5.43; Cl, 13.75%. Found: C, 70.15; H, 4.74; N, 5.39; Cl, 13.69%.

DESCRIPTION 6

1-(2-Fluorophenyl)-1,4-dihydroisoquinol-3-one

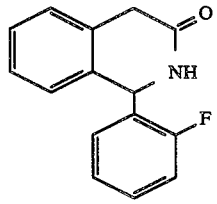

m.p. 167°–169° C. (from ethanol).

Analysis: Found C, 74.56; H, 5.16; N, 5.68%. $C_{15}H_{12}NOF$ requires C, 74.68; H, 5.01; H, 5.81%.

DESCRIPTION 7

1-(4-Bromophenyl)-1,4-dihydroisoquinol-3-one

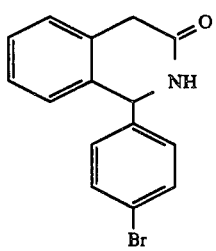

m.p. 187°–192° C. (from ethanol).
Analysis: Found C, 59.29; H, 3.88; N, 4.55. $C_{15}H_{12}NOBr$ requires C, 59.62; H, 4.00; N, 4.64.

DESCRIPTION 8

1-(2-Chloro-6-methylphenyl)-1,4-dihydroisoquinol-3-one

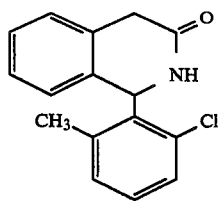

From 2-chloro-6-methylbenzaldehyde[1] and benzyl cyanide m.p. 248°–251° C. (Ethyl acetate/ethanol/ether).

[1] Jolad S. D. et al Naturwissenschaften 48, 645 (1961) Beech W. F. J. Chem. Soc. 1297, (1954).

DESCRIPTION 9

1(2-Methanesulphonylphenyl)-1,4-dihydroisoquinol-3-one

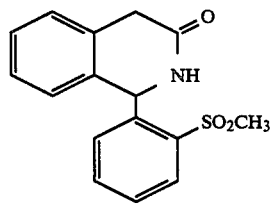

From 2-methanesulphonylbenzaldehyde[2] and benzyl cyanide m.p. 205°–210° C. (Ethyl acetate/ethanol/ether).

[2] Eistert et al. Chem. Ber. 1964, 97, 1470.

DESCRIPTION 10

1-(3-Methoxy-4-chlorophenyl)-1,4-dihydroisoquinol-3-one

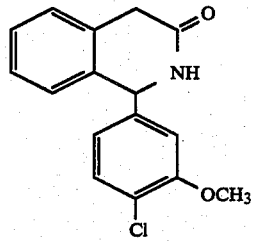

From 3-methoxy-4-chlorophenylbenzaldehyde[3] and benzyl cyanide m.p. 134°-7° C. (Ethyl acetate/ethanol/ether).

[3] Faith H. E. et al, J. Am. Chem. Soc. 1955 77, 543.

DESCRIPTION 11

7-Chloro-1-(4-chlorophenyl)-1,4-dihydroisoquinol-3-one

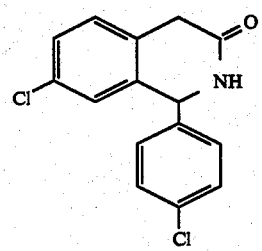

m.p. 157°-158° C. (from ether).

Analysis: $C_{15}H_{11}NOCl_2$ requires C, 61.67; H, 3.80; N, 4.79; Cl, 24.32%. Found: C, 61.66; H, 3.73; N, 4.89; Cl, 24.35%.

DESCRIPTION 12

1-(4-Chlorophenyl)-7-fluoro-1,4-dihydroisoquinol-3-one

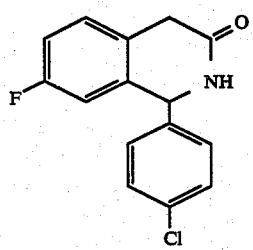

m.p. 131°-133° C. (from ether/pentane).

DESCRIPTION 13

1-(4-Chlorophenyl)-6-fluoro-1,4-dihydroisoquinol-3-one

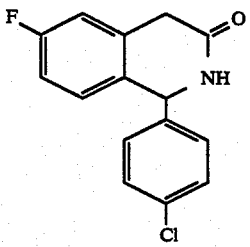

m.p. 160°-161° C. (from ethyl acetate/60°-80° C. petroleum ether).

Analysis: $C_{15}H_{11}NOClF$ requires C, 65.35; H, 4.02; N, 5.08%. Found: C, 65.33; H, 3.99; N, 5.03%.

DESCRIPTION 14

1-(4-Chlorophenyl)-5-fluoro-1,4-dihydroisoquinol-3-one

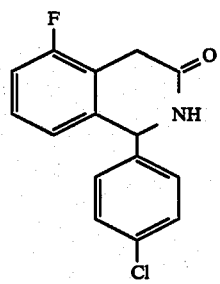

m.p. 194°-196° C. (from ether).

DESCRIPTION 15

1-(4-Chlorophenyl)-6,7-dimethoxy-1,4-dihydroisoquinol-3-one

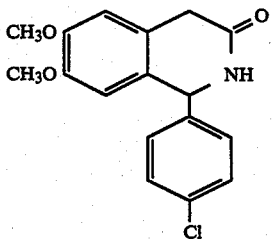

m.p. 185°-187° C. (from ethanol).

Analysis: $C_{17}H_{16}NO_3Cl$ requires C, 64.25; H, 5.05; N, 4.4; Cl, 11.15%. Found: C, 64.75; H, 5.0; N, 4.45; Cl, 11.4%.

1-(4-Chlorophenyl)-6-methoxy-1,4-dihydroisoquinol-3-one (DESCRIPTION 16) and 1-(4-chlorophenyl)-8-methoxy-1,4-dihydroisoquinol-3-one (DESCRIPTION 17)

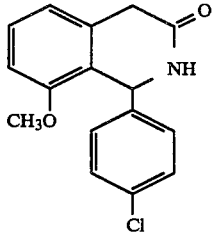

(DESCRIPTION 16)

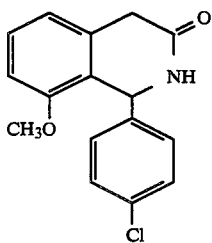

(DESCRIPTION 17)

A mixture of 3-methoxyphenylacetonitrile (25 g) and polyphosphoric acid (110 g) was heated and stirred at 90°-110° C. for 45 mins. 4-Chlorobenzaldehyde (12 g) was added in portions over 25 mins., with vigorous stirring. The mixture was heated at 120°-130° C. for 3 h, cooled and poured into a mixture of 0.88 ammonium hydroxide (2.5 liters) and 10% sodium hydroxide (200 ml), and left overnight. The precipitate was filtered off, washed with water, dissolved in chloroform (150 ml) and chromatographed on silica gel (500 g) using 1:1 ethyl acetate-pentane as the eluent. Recovery of the first band to be eluted, followed by recrystallisation from chloroform-pentane, afforded 1-(4-chlorophenyl)-8-methoxy-1,4-dihydroisoquinol-3-one (DESCRIPTION 17), 1.2 g, m.p. 250°-251° C.

H.R.M.S. $C_{16}H_{14}NO_2Cl$ requires 287.0712. Found: 287.0714.

NMR CDCl$_3$ δ 3.58 (2H, s), 3.80 (3H, s), 5.85 (1H, brd), 6.7–6.9 and 7.1–7.4 (7H, m).

Recovery of the second band, followed by recrystallisation from ethyl acetate-pentane, afforded 1-(4-chlorophenyl)-6-methoxy-1,4-dihydroisoquinol-3-one (DESCRIPTION 16) 6.8 g, m.p. 200°-201° C.

H.R.M.S. $C_{16}H_{14}NO_2Cl$ requires 287.0712. Found: 287.0717.

Analysis: Found: C, 66.8; H, 4.9; N, 4.65; Cl, 12.65%. $C_{16}H_{14}NO_2Cl$ requires C, 66.8; H, 4.9; N, 4.8 Cl, 12.32%.

NMR CDCl$_3$ δ 3.58 (2H, s), 3.75 (3H, s), 5.55 (1H, br.s), 6.6–7.4 (7H, m).

DESCRIPTION 18

1-(4-Chlorophenyl)-6,7-methylenedioxy-1,4-dihydroisoquinol-3-one

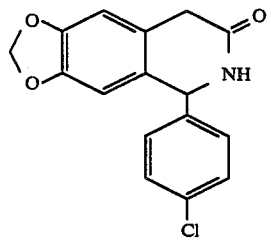

A flask containing polyphosphoric ester (90 g) was held at 100° C. (oil bath temperature). A mixture of 3,4-methylenedioxyphenylacetamide (22 g, 123 mmol) and parachlorobenzaldehyde (17.1 g, 122 mmol) was added in three portions over half an hour, with stirring. The solution (dark red) was heated at 100° C. for 5 h and poured onto ice (400 ml). A 10% solution (aqueous) of sodium carbonate (2 liters) was added and the mixture was left overnight. The resulting oily gum was extracted with chloroform (2×500 ml) and the chloroform extracts washed with brine (50 ml) and dried over sodium sulphate. The chloroform solution was filtered and the solvent was removed under reduced pressure. The solid so formed was triturated with ethanol (2×30 ml) to give 1-(4-chlorophenyl)-6,7-methylenedioxy-1,4-dihydroisoquinol-3-one (7 g). The combined ethanol layers were evaporated under reduced pressure and the residue chromatographed (Silica gel (300 g), chloroform as eluent) to give a further 8 g of product. Total yield (15 g, 41%), m.p. 200°-202° C. (ethanol).

Analysis: $C_{16}H_{12}NO_3Cl$ requires C, 63.69; H, 4.01; N, 4.64; Cl, 11.75%. Found: C, 63.45; H, 3.91; N, 4.55; Cl, 11.99%.

DESCRIPTION 19

1-(2-Chlorophenyl)-6,7-methylenedioxy-1,4-dihydroisoquinol-3-one

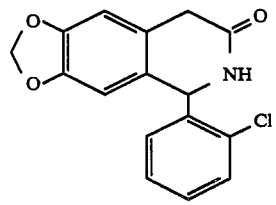

This compound was prepared in an analogous manner to that described in DESCRIPTION 18, from 3,4-methylenedioxyphenylacetonitile and 2-chlorobenzaldehyde. m.p. 207°-9° C. (Ethanol).

Analysis: $C_{16}H_{12}NO_3Cl$ requires C, 63.69; H, 4.01; N, 4.64; Cl, 11.75%. Found: C, 63.37; H, 4.19; N, 4.59; Cl, 11.93%.

DESCRIPTION 20

1-(2-Chlorophenyl)-6-methoxy-1,4-dihydroisoquinol-3-one and DESCRIPTION 21

1-(2-Chlorophenyl)-8-methoxy-1,4-dihydroisoquinol-3-one

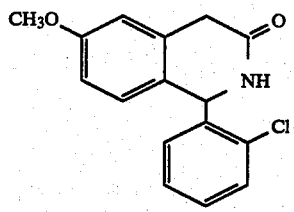
(DESCRIPTION 20)

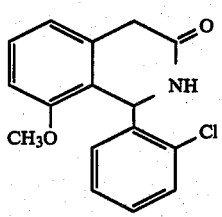
(DESCRIPTION 21)

A mixture of 3-methoxyphenylacetamide (55 g, 333 mmol) (formed from 3-methoxyphenylacetylchloride and concentrated aqueous ammonia solution), 2-chlorobenzaldehyde (46 g, 329 mmol) and polyphosphoric ester (400 g) were stirred at 100° C. (oil bath temperature) for 5 h. The mixture was poured onto ice (500 g) and 0.880 ammonia (3 liters) was added. The mixture was left overnight. The mixture was warmed on a water bath for 3 h (at 60° C.), cooled and extracted with chloroform (3×400 ml). The combined chloroform extracts were washed with water (100 ml) and brine (300 ml) and dried over sodium sulphate. Removal of the solvent under reduced pressure gave a dark red/brown oil (90 g). This material was chromatographed (Silica gel, chloroform as eluent) to give 1-(2-chlorophenyl)-8-methoxy-1,4-dihydroisoquinol-3-one (2.8 g) (eluted first):

m.p. 230°–3° C. (ethanol).

Analysis: $C_{16}H_{14}NO_2Cl$ requires C, 66.79; H, 4.90; N, 4.87; Cl, 12.37%. Found: C, 66.77; H, 4.92; N, 4.84; Cl, 12.42%.

Further elution gave 1-(2-chlorophenyl)-6-methoxy-1,4-dihydroisoquinol-3-one (7.5 g):

m.p. 203°–5° C. (ethanol).

Analysis: $C_{16}H_{14}NO_2Cl$ requires C, 66.79; H, 4.90; N, 4.87; Cl, 12.37%. Found: C, 66.78; H, 4.88; N, 4.82; Cl, 11.55%.

DESCRIPTION 22

1-(4-Cyanophenyl)-1,4-dihydroisoquinol-3-one

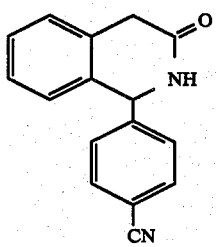

A solution of 1-(4-bromophenyl)-1,4-dihydroisoquinol-3-one (15.1 g, 50 mmol) and cuprous cyanide (8.95 g, 100 mmol) in N-methylpyrrolidinone (150 ml) was heated under reflux under a nitrogen atmosphere for 2 h. The solution was cooled and diluted with 10% aqueous ethylenediamine solution (1000 ml), then extracted with ethyl acetate (4×250 ml). The combined extracts were washed with water (4×250 ml) and brine (250 ml), then dried (MgSO$_4$) and evaporated to dryness to leave a pale brown solid which was crystallised from ethyl acetate to give the title compound (8.43 g, 68%), m.p. 165°–168° C. (ethanol).

Analysis: Found: C, 77.10; H, 4.88; N, 11.04. $C_{16}H_{12}N_2O$ requires C, 77.40; H, 4.87; N, 11.28.

i.r. $\nu$max (CHCl$_3$) 2240 cm$^{-1}$.

DESCRIPTION 23

1-(3-Methanesulphonamidophenyl)-1,4-dihydroisoquinol-3-one hemihydrate

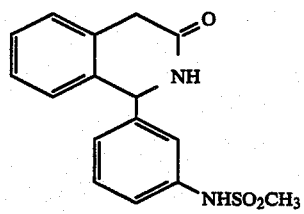

A mixture of 1-(3-nitrophenyl)-1,4-dihydroisoquinol-3-one (12.2 g) and 5% palladium-carbon (3 g) in ethylacetate (400 ml) was hydrogenated at room temperature and pressure until uptake of hydrogen ceased. The mixture was filtered (celite), and the filtrate evaporated to dryness to give 1-(3-aminophenyl)-1,4-dihydroisoquinol-3-one (9.0 g), m.p. 179°–180° C. which was used without purification.

A solution of 1-(3-aminophenyl)-1,4-dihydroisoquinol-3-one (8.0 g) in dichloromethane (500 ml) and triethylamine (50 ml) was treated dropwise, at room temperature, with a solution of mesyl chloride (9.7 g) in dichloromethane (20 ml). After stirring for 3 h, the resulting precipitate (m.p. 251°–253° C.) was collected, washed with dichloromethane, water, and air dried. The product was stirred with a mixture of 10% aqueous sodium hydroxide (200 ml) and methanol (20 ml) at 50° C. for 1 h. The mixture was filtered and the filtrate was evaporated to one third volume in vacuo. It was acidified with dilute hydrochloric acid, and the resulting precipitate was collected and washed with water. Recrystallisation from methanol-ether afforded the title compound (3.55 g)

m.p. 106°–108° C.

Analysis: $C_{16}H_{16}N_2O_3S$ 0.5H$_2$O requires C, 59.05; H, 5.25; N, 8.6%. Found: C, 59.05; H, 5.3; N, 8.3%.

DESCRIPTION 24

1-(2-Chloro-6-fluorophenyl)-8-methoxy-1,4-dihydroisoquinol-3-one

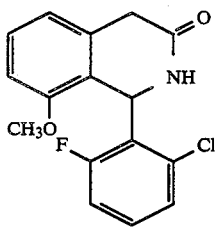

m.p. 266°–269° C.

Analysis: $C_{16}H_{13}NO_2ClF$ requires C, 62.86; H, 4.29; N, 4.58; Cl, 11.60%. Found: C, 62.54; H, 4.25; N, 4.48; Cl, 11.45%.

DESCRIPTION 25

1-(2-Chloro-6-fluorophenyl)-6-methoxy-1,4-dihydroisoquinol-3-one

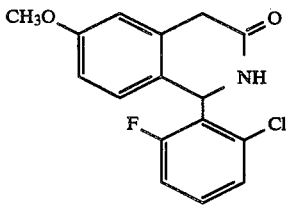

m.p. 221°–224° C.

Analysis: $C_{16}H_{13}NO_2ClF$ requires C, 62.86; H, 4.29; N, 4.58; Cl, 11.60%. Found: C, 62.76; H, 4.26; N, 4.53; Cl, 11.94%.

EXAMPLE 1

1-(2-Chlorophenyl)-3-dimethylamino-1,4-dihydroisoquinoline hydrochloride

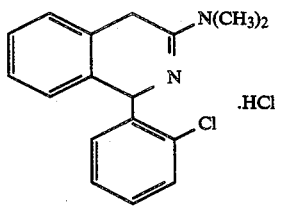

1-(2-Chlorophenyl)-1,4-dihydroisoquinol-3-one (11.0 g, 43 mmol) was dissolved in dimethylcarbamyl chloride (50 g) on an oil bath (bath temperature 160°–170° C.) for 1 and three quarter hours. The mixture was cooled, evaporated under reduced pressure and partitioned between water (150 ml), 5M hydrochloric acid, ethyl acetate (100 ml) and chloroform (100 ml). The organic layer was separated and extracted with a portion of water (50 ml). The combined aqueous extracts were washed with ethyl acetate (3×25 ml) and basified (10% sodium hydroxide) to pH 14. The oil so formed was extracted with ethyl acetate (2×100 ml) and the combined ethyl acetate layers were washed with brine (50 ml) and dried over sodium sulphate. The solution was filtered and reduced to 100 ml under reduced pressure. Ethereal hydrogen chloride was added to precipitate the salt. After trituration, the solid was filtered off and dried in the vacuum over (90° C., 1 mm). This gave 1-(2-chlorophenyl)-3-dimethylamino-1,4-dihydroisoquinoline hydrochloride (5.7 g, 42%) m.p. 162°–6° C. (soften then hardened and remelted 252°–5° C.). I.R. $\nu$max (Nujol) 1650 cm$^{-1}$.

NMR (CDCl$_3$/DMSO) $\delta$ 3.23, 3.40 (2×3H, s), 4.36 (2H, b), 6.32 (1H, b), 6.6–7.6 (8H, m), 10.20 (1H, b).

H.R.M.S. $C_{17}H_{17}N_2Cl$ requires 284.1080. Found: 284.1084.

Analysis: C17H18N2Cl2 requires C, 58.47; H, 5.94; N, 7.18%. Found: C, 58.35; H, 6.05; N, 7.30%.

The following examples (2–29) were prepared in a similar manner to that described for Example 1.

EXAMPLE 2

1-(4-Chlorophenyl)-3-dimethylamino-1,4-dihydroisoquinoline hydrochloride hydrate

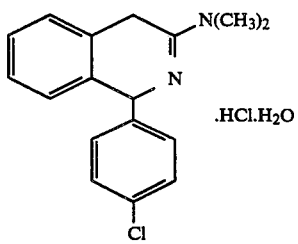

m.p. 136°–139° C. (from ethanol-ether).

Analysis: $C_{17}H_{17}N_2ClHCl.H_2O$ requires C, 60.2; H, 5.95; N, 8.25; Cl, 20.9%. Found: C, 60.1; H, 5.8; N, 8.35; Cl, 21.55%.

EXAMPLE 3

1-(4-Nitrophenyl)-3-dimethylamino-1,4-dihydroisoquinoline hydrochloride hemihydrate

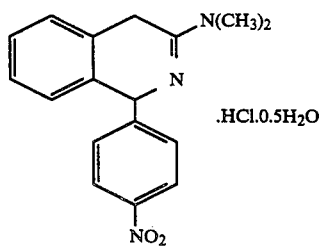

m.p. 153°–157° C. (from ethanol-ether).

Analysis: $C_{17}H_{17}N_3O_2HCl_{0.5}H_2O$ requires C, 59.9; H, 5.6; N, 12.3; Cl, 10.4%. Found: C, 60.05; H, 5.45; N, 12.0; Cl, 10.45%.

EXAMPLE 4

1-(2-Bromophenyl)-3-dimethylamino-1,4-dihydroisoquinoline hydrochloride hemihydrate

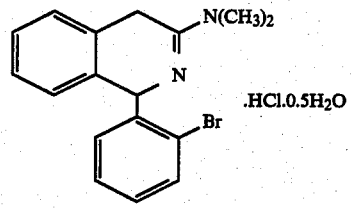

m.p. 241°–244° C. (ethanol/dichloroethane/ethyl acetate).

Analysis: $C_{17}H_{18}N_2ClBr \cdot 0.5H_2O$ requires C, 54.49; H, 5.11; N, 7.48%. Found: C, 54.60; H, 4.94; N, 7.53%.

EXAMPLE 5

1-(2-Trifluoromethylphenyl)-3-dimethylamino-1,4-dihydroisoquinoline hydrochloride

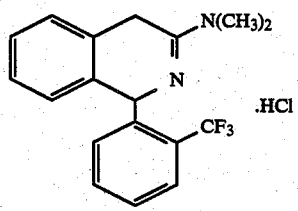

m.p. 248°–251° C. (dichloroethane/chloroform/ethyl acetate).

Analysis: $C_{18}H_{18}N_2ClF_3$ requires C, 60.93; H, 5.11; N, 7.9%. Found: C, 60.80; H, 5.09; N, 7.88%.

EXAMPLE 6

1-(2,4-Dichlorophenyl)-3-dimethylamino-1,4-dihydroisoquinoline hydrochloride

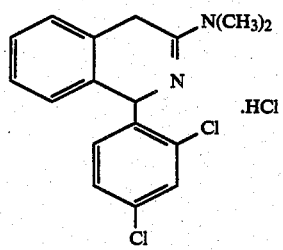

m.p. 220°–222° C. (dichloroethane/toluene).

Analysis: $C_{17}H_{17}N_2Cl_3$ requires C, 57.4; H, 4.82; N, 7.88%. Found: C, 57.35; H, 4.98; N, 7.66%.

EXAMPLE 7

1-(2,6-Dichlorophenyl)-3-dimethylamino-1,4-dihydroisoquinoline hydrochloride

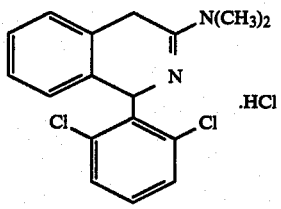

m.p. 263°–274° C. (with decomposition) (ethanol/dichloroethane/ethyl acetate).

Analysis: $C_{17}H_{17}N_2Cl_3$ requires C, 57.4; H, 4.82; N, 7.88; Cl, 30.08%. Found: C, 57.21; H, 4.64; N, 7.70; Cl, 29.99%.

EXAMPLE 8

1-(2-Chloro-6-fluorophenyl)-3-dimethylamino-1,4-dihydroisouinoline hydrochloride

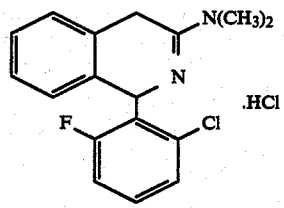

m.p. 262°–265° C. (dichloroethane/ethanol/ethyl acetate).

Analysis: $C_{17}H_{17}N_2Cl_2F$ requires C, 60.19; H, 5.05; N, 8.26; Cl, 21.01%. Found: C, 59.92; H, 5.11; N, 8.19; Cl, 21.36%.

EXAMPLE 9

1-(3-Chlorophenyl)-3-dimethylamino-1,4-dihydroisoquinoline hydrochloride

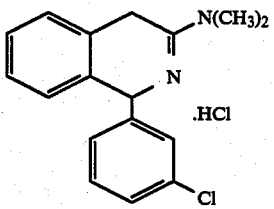

m.p. 204°–6° C. (dichloroethane/toluene).

Analysis: $C_{17}H_{18}N_2Cl_2$ requires C, 63.56; H, 5.65; N, 8.72%. Found: C, 63.28; H, 5.44; N, 8.55%.

EXAMPLE 10

1-(2-Fluorophenyl)-1,4-dihydro-3-dimethylaminoisoquinoline hydrochloride

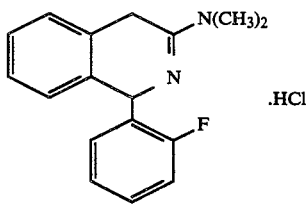

m.p. 261°–265° C. (from dichloromethane/ethyl acetate).

Analysis: Found: C, 66.51; H, 6.00; N, 9.31; Cl, 11.50%. $C_{17}H_{18}N_2ClF$ requires C, 66.99; H, 5.95; N, 9.19; Cl, 11.63%

EXAMPLE 11

1-(4-Bromophenyl)-1,4-dihydro-3-dimethylaminoisoquinoline hydrochloride hydrate

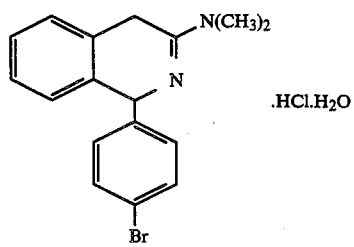

m.p. 137°–141° C. (from dichloroethane/ethyl acetate).

Analysis: Found: C, 53.16; H, 5.05; N, 6.94; Cl, 9.16%. $C_{17}H_{18}N_2BrCl.H_2O$ requires C, 53.20; H, 5.25; N, 7.30; Cl. 9.24%.

EXAMPLE 12

1-(2-Chloro-6-methylphenyl)-3-dimethylamino-1,4-dihydroisoquinoline

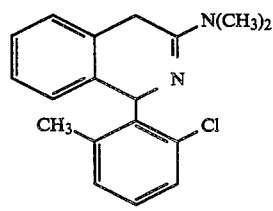

m.p. 153°–4° C. (Ethanol/ethyl acetate).
Analysis: $C_{18}H_{19}N_2Cl$ requires C, 72.35; H, 6.41; N, 9.37% Found: C, 72.41; H, 6.38; N, 9.32%.

EXAMPLE 13

1-(2-Chloro-3-methylphenyl)-3-dimethylamino-1,4-dihydroisoquinoline hydrochloride hemihydrate

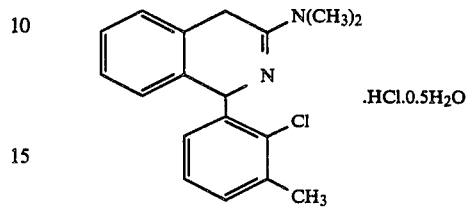

Formed from 1-(2-chloro-3-methylphenyl)-1,4-dihydroisoquinol-3-one (which used as the crude product formed from 2-chloro-3-methylbenzaldehyde and phenyl cyanide).

m.p. 256°–8° C. (Ethanol/ethyl acetate).

Analysis: $C_{18}H_{20}N_2Cl_2.0.5H_2O$ requires C, 62.79; H, 6.15; N, 8.14%. Found: C, 63.06; H, 6.08; N, 8.04%.

EXAMPLE 14

1-(3-Methoxy-4-chlorophenyl)-3-dimethylamino-1,4-dihydroisoquinoline hydrochloride

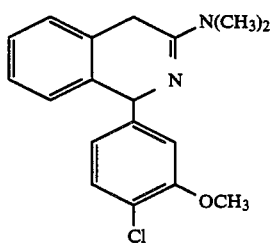

m.p. 223°–6° C. (ethanol/ethyl acetate).

EXAMPLE 15

1-(2-Methanesulphonylphenyl)-3-dimethylamino-1,4-dihydroisoquinoline hydrochloride

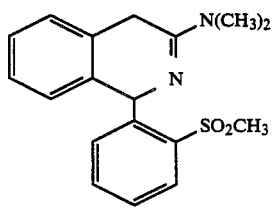

m.p. 294°–7° C. (ethanol/ethyl acetate).

EXAMPLE 16

1-(4-Methanesulphonylphenyl)-3-dimethylamino-1,4-dihydroisoquinoline hydrochloride

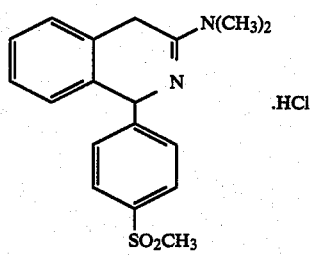

This was prepared from 1-(4-methanesulphonylphenyl)-1,4-dihydroisoquinol-3-one (which was used as the crude product formed from 4-methanesulphonylbenzaldehyde and phenyl cyanide).

m.p. 265°–7° C. (ethanol/ethyl acetate).

Analysis: $C_{18}H_{21}N_2O_2SCl$ requires C, 59.25; H, 5.80; N, 7.68; Cl, 9.72; S, 8.79%. Found: C, 59.47; H, 5.89; N, 7.71; Cl, 9.91; S, 8.62%.

EXAMPLE 17

1-(4-Cyanophenyl)-1,4-dihydro-3-dimethylaminoisoquinoline hydrochloride hydrate

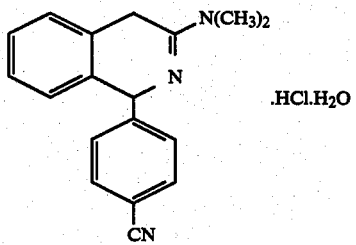

m.p. 216°–222° C.

Analysis: Found: C, 65.66; H, 5.74; N, 12.76; Cl, 10.78% $C_{18}H_{18}N_3Cl.H_2O$ requires C, 65.54; H, 6.11; N, 12.74; Cl, 10.75%.

i.r. $\nu$max (nujol) 2240 cm$^{-1}$.

EXAMPLE 18

1-(4-Chlorophenyl)-3-dimethylamino-7-methyl-1,4-dihydroisoquinoline hydrochloride hemihydrate

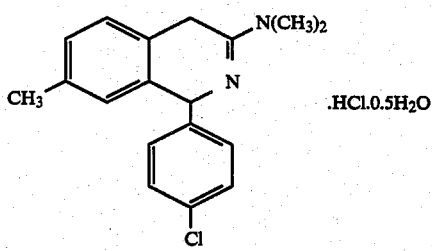

m.p. 134°–142° C. (ethanol/ether).

Analysis: $C_{18}H_{19}N_2Cl.HCl.0.5H_2O$ requires C, 62.8; H, 6.15; N, 8.15; Cl, 20.6%. Found: C, 62.9; H, 6.0; N, 7.75; Cl, 20.3%.

EXAMPLE 19

3-Dimethylamino-1-phenyl-1,4-dihydroisoquinoline hydrochloride hemihydrate

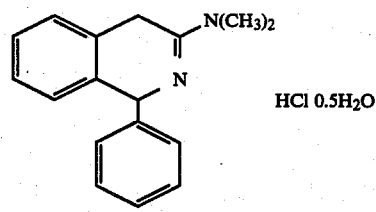

m.p. 265°–268° C. (ethanol/ether).

Analysis: $C_{17}H_{18}N_2.HCl.0.5H_2O$ requires C, 69.0; H, 6.8; N, 9.5%. Found: C, 68.75; H, 6.6; N, 9.4%.

EXAMPLE 20

7-Chloro-1-(4-chlorophenyl)-3-dimethylamino-1,4-dihydroisoquinoline hydrochloride hemihydrate

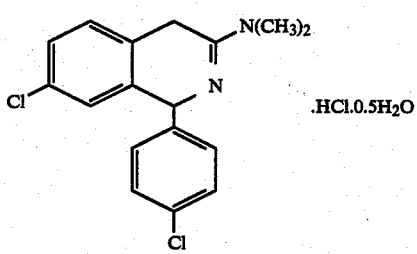

m.p. 226°–228° C. (from ethyl acetate/ether).

Analysis: $C_{17}H_{16}N_2Cl_2.HCl.0.5H_2O$ requires C, 55.97; H, 4.94; N, 7.68%. Found: C, 55.66; H, 4.75; N, 7.76%.

EXAMPLE 21

1-(4-Chlorophenyl)-3-dimethylamino-7-fluoro-1,4-dihydroisoquinoline hydrochloride hydrate (1.5)

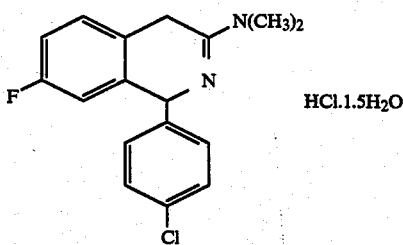

m.p. 215°–218° C. (from ethyl acetate/ether).

Analysis: $C_{17}H_{16}N_2ClF.HCl.1.5H_2O$ requires C, 55.74; H, 5.46; N, 7.65%. Found: C, 55.56; H, 5.25; N, 7.80%.

EXAMPLE 22

1-(4-Chlorophenyl)-3-dimethylamino-6-fluoro-1,4-dihydroisoquinoline hydrochloride hydrate (1.5)

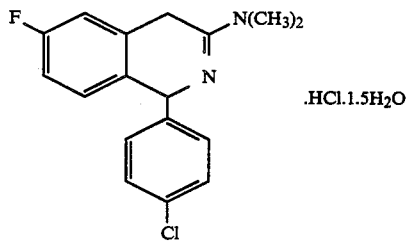

m.p. 143°–6° C. (from ether/ethyl acetate).

Analysis: $C_{17}H_{16}N_2ClF.HCl.1.5.H_2O$ requires C, 55.74; H, 5.46; N, 7.65%. Found: C, 55.44; H, 5.33; N, 7.45%.

EXAMPLE 23

1-(4-Chlorophenyl)-3-dimethylamino-6,7-dimethoxy-1,4-dihydroisoquinoline hydrochloride hemihydrate

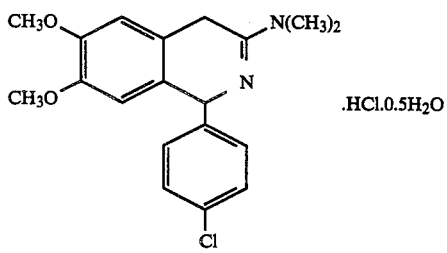

m.p. 134°–138° C. (dichloromethane/toluene).

Analysis: $C_{19}H_{22}N_2O_2Cl_2.0.5H_2O$ requires C, 58.47; H, 5.94; N, 7.18%. Found: C, 58.35; H, 6.05; N, 7.30%.

EXAMPLE 24

1-(4-Chlorophenyl)-3-dimethylamino-8-methoxy-1,4-dihydroisoquinoline hydrochloride

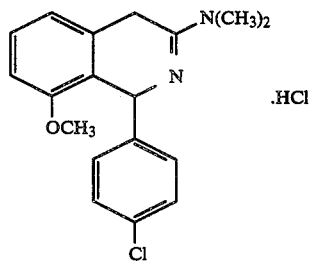

NMR CDCl$_3$ δ 3.32 (6H, d), 3.65 (3H, s), 3.80 (2H, q), 6.37 (1H, d), 6.6–7.5 (7H, m).

EXAMPLE 25

1-(4-Chlorophenyl)-3-dimethylamino-6-methoxy-1,4-dihydroisoquinoline hydrochloride hydrate

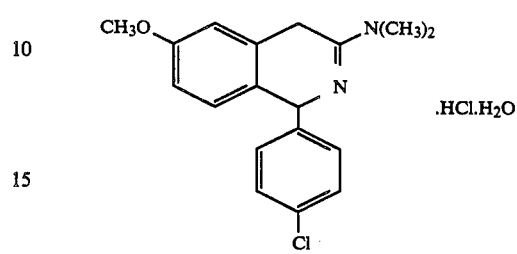

m.p. 145°–150° C. (from methanol-ether).

Analysis: Found: C, 58.6; H, 5.95; N, 7.55; Cl, 19.2%. $C_{18}H_{19}N_2Cl.HCl.H_2O$ requires C, 58.55; H, 6.0; N, 7.6; Cl. 19.2%.

EXAMPLE 26

1-(2-Chlorophenyl)-3-dimethylamino-6-methoxy-1,4-dihydroisoquinoline hydrochloride hydrate

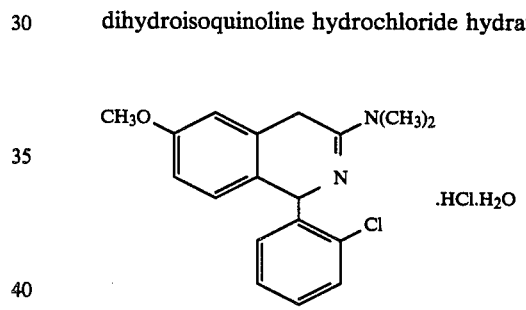

m.p. 158°–60° C. (toluene/dichloroethane).

Analysis: $C_{18}H_{20}N_2OCl_2.H_2O$ requires C, 58.54; H, 6.01; N, 7.58%. Found: C, 58.20; H, 5.63; N, 7.29%.

EXAMPLE 27

1-(2-Chlorophenyl)-3-dimethylamino-8-methoxy-1,4-dihydroisoquinoline hydrochloride hemihydrate

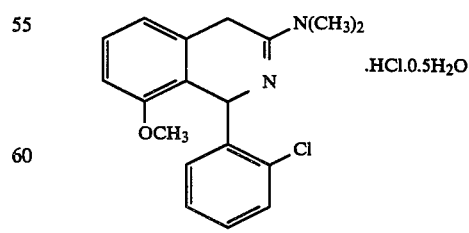

Sublimes 210° C.

Analysis: $C_{18}H_{20}N_2OCl_2.0.5H_2O$ requires C, 60.01; H, 5.88; N, 7.77%. Found: C, 60.07; H, 5.56; N, 7.87%.

EXAMPLE 28

1-(4-Chlorophenyl)-3-dimethylamino-6,7-methylenedioxy-1,4-dihydroisoquinoline hydrochloride hemihydrate

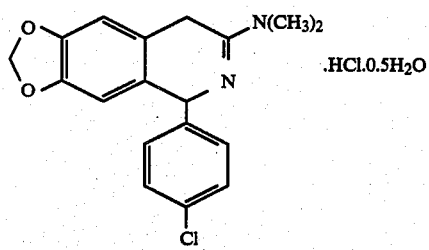

m.p. 212°–5° C. (dichloroethane/toluene).
Analysis: $C_{18}H_{18}N_2O_2Cl_2.0.5H_2O$ requires C, 57.77; H, 5.12; N, 7.48%. Found: C, 57.66; H, 5.21; N, 7.31%.

EXAMPLE 29

1-(2-Chlorophenyl)-3-dimethylamino-6,7-methylenedioxy-1,4-dihydroisoquinoline hydrochloride

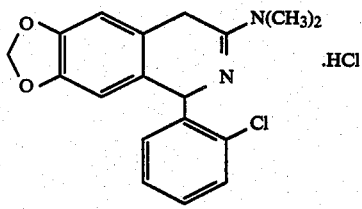

m.p. 195°–8° C. (dichloroethane).
NMR δ (DMSO/CDCl₃) 3.4(6H), 4.15(2H), 5.8(1H), 5.95(2H), 6.5(1H), 6.8(1H), 7.35(4H).
HRMS $C_{18}H_{17}N_2O_2Cl$ requires 328.0979, found: 328.0983.

EXAMPLE 30

1-(4-Chlorophenyl)-6,7-dihydroxy-3-dimethylamino-1,4-dihydroisoquinoline hydrobromide

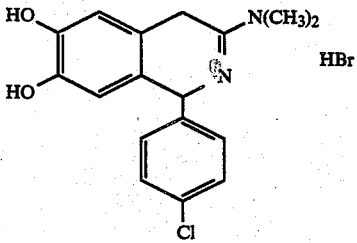

A solution of 1-(4-chlorophenyl)-3-dimethylamino-6,7-dimethoxy-1,4-dihydroisoquinoline hydrochloride (1.3 g) in 48% aqueous hydrobromic acid (100 ml) was heated at 100°–120° C. under nitrogen for 3 h. The hot solution was filtered, and the filtrate evaporated to dryness in vacuo and recrystallised from ethanol-ether, to give 1-(4-chlorophenyl)-6,7-dihydroxy-3-dimethylamino-1,4-dihydroisoquinoline hydrobromide (1.07 g), m.p. 232°–235° C.
Analysis: $C_{17}H_{17}N_2O_2Cl.HBr$ requires C, 51.35; H, 4.55; N, 7.05; Cl, 8.9; Br, 20.1%. Found: C, 51.25; H, 4.2; N, 6.9; Cl, 8.5; Br, 19.9%.

EXAMPLE 31

1-(4-Chlorophenyl)-3-dimethylamino-8-hydroxy-1,4-dihydroisoquinoline hydrobromide hydrate

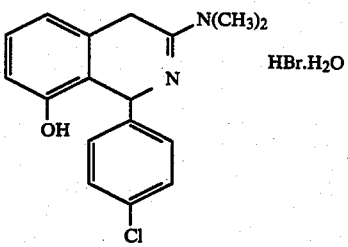

A solution of 1-(4-chlorophenyl)-3-dimethylamino-8-methoxy-1,4-dihydroisoquinoline hydrochloride (0.9 g) in 48% aqueous hydrobromic acid (100 ml) was heated at 115°–120° C. for 2.5 h. The solution was evaporated to dryness in vacuo and recrystallised from methanol-water to afford the title compound, (0.66 g), m.p. 185°–187° C.
Analysis: Found: C, 51.05; H, 4.55; N, 6.85%. $C_{17}H_{17}N_2ClO.HBr.H_2O$ requires C, 51.1; H, 5.05; N, 7.01%.

EXAMPLE 32

1-(4-Chlorophenyl)-3-dimethylamino-6-hydroxy-1,4-dihydroisoquinoline hydrobromide

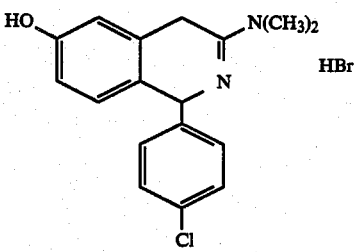

A solution of 1-(4-chlorophenyl)-3-dimethylamino-6-methoxy-1,4-dihydroisoquinoline hydrochloride hydrate (1.5 g) in 48% aqueous hydrobromic acid (200 ml) was heated at 120° C. for 2.5 h. The solution was evaporated to dryness in in vacuo and recrystallised from ethanol-ether to give the title compound, (2.53 g), m.p. 260°–264° C.
Analysis: Found: C, 53.25; H, 4.75; N, 7.25%. $C_{17}H_{17}N_2ClO.HBr$ requires C, 53.5; H, 4.75; N, 7.35%.

The following examples (33 and 34) were prepared in a similar manner to that described for Example 30.

EXAMPLE 33

1-(2-Chlorophenyl)-3-dimethylamino-6-hydroxy-1,4-dihydroisoquinoline hydrobromide

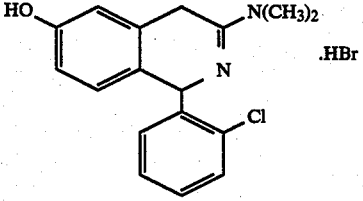

m.p. 301°–2° C. (methanol/ethyl acetate).

Analysis: $C_{17}H_{18}N_2OClBr$ requires C, 53.49; H, 4.75; N, 7.34; Br, 20.97%. Found: C, 53.31; H, 4.68; N, 7.23; Br, 20.91%.

EXAMPLE 34

1-(2-Chlorophenyl)-3-dimethylamino-8-hydroxy-1,4-dihydroisoquinoline hydrobromide hemihydrate

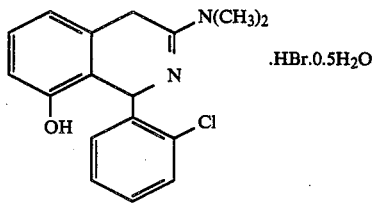

m.p. >320° C. (dec) (methanol/ethyl acetate).

Analysis: $C_{17}H_{18}N_2OClBr.0.5H_2O$ requires C, 52.26; H, 4.90; N, 7.17%. Found: C, 52.56; H, 5.26; N, 6.79%.

EXAMPLE 35

1-(4-Chlorophenyl)-3-dimethylamino-6,7-bis(dimethylcarbamoyl)-1,4-dihydroisoquinoline hydrochloride

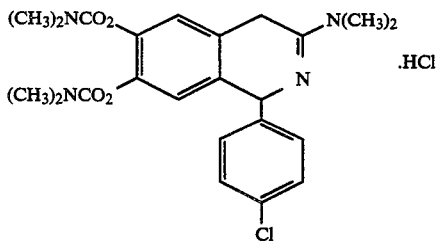

To dimethylcarbamoyl chloride (100 ml) was added 1-(4-chlorophenyl)-3-dimethylamino-6,7-dihydroxy-1,4-dihydroisoquinoline hydrobromide (4.5 g, 11 mmol) and the mixture was heated at 150° C. (oil bath temperature) for 3½ h under a very slow stream of nitrogen. The solution was cooled and the excess dimethylcarbamoyl chloride was removed under reduced pressure. The residue was dissolved in 0.5M hydrochloric acid (100 ml) and extracted with ethyl acetate. The ethyl acetate layer was discarded and the aqueous layer was brought to pH 11 with 10% aqueous sodium carbonate solution. The oily mixture was extracted with ethyl acetate (2×100 ml), the combined organic layers were washed with brine, dried over sodium sulphate and evaporated to one third volume. Ethereal hydrogen chloride was added and the solvent was removed under reduced pressure. The residue was dissolved in dichloroethane (30 ml) and filtered. The solution was evaporated under reduced pressure to give the desired product (2.3 g, 41%).

i.r. $cm^{-1}$ 1645, 1730.

NMR δ cdcl₃ 3.0 (12H), 3.4 (6H), 3.9 (2H), 6.15 (1H), 7.0–7.4 (6H).

HRMS $C_{23}H_{27}N_4O_4Cl$ requires 458.1720, found 458.1713.

EXAMPLE 36

1-(4-Chlorophenyl)-3-n-propylamino-1,4-dihydroisoquinoline hydrochloride

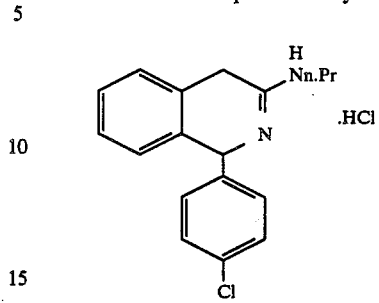

1-(4-Chlorophenyl)-1,4-dihydroisoquinol-3-one (6.2 g, 24 mmol) was dissolved in dry methylene chloride (30 ml) and stirred under nitrogen. A solution of triethyloxonium tetrafluoroborate in methylene chloride (1M), (24 ml) was added in one portion at room temperature. After 3 h at room temperature, a solution of n-propylamine (2.0 g, 34 mmol) in ethanol (20 ml) was added and the mixture refluxed for 24 h. The solution was cooled, the solvent removed under reduced pressure and the residue partitioned between ethyl acetate (200 ml) and 10% sodium hydroxide (100 ml). The organic layer was separated, acidified with 5M sulphuric acid (2×50 ml) and washed with water (100 ml). The combined aqueous phases were basified (Care) with 10% sodium hydoxide and the oil so produced extracted with ethyl acetate (2×100 ml). The combined ethyl acetate layers were washed with brine (50 ml) and dried over sodium sulphate. The solution was filtered and reduced to 100 ml under reduced pressure. Ethereal hydrogen chloride was added and the solvent was removed under reduced pressure. Toluene (50 ml) was added to the foam so produced and evaporated off. The foam that remained was dried in the vacuum over (90° C., 1 mm) to give 1-(4-chlorophenyl)-3-n-propylamino-1,4-dihydroisoquinoline hydrochloride (3.1 g, 38%).

I.R. νmax (Nujol) 1660 $cm^{-1}$.

NMR CDCl₃ δ 0.92 (3H, t), 1.7 (2H, m), 3.2–4.7 (4H, m), 5.96 (1H, m), 6.8–7.4 (8H, m), 10.2 (b).

The following example was prepared in a similar manner to that described in Example 36.

EXAMPLE 37

1-(4-Chlorophenyl)-3-morpholino-1,4-dihydroisoquinoline hydrochloride monohydrate

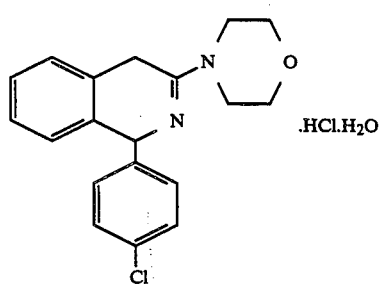

m.p. 209°–210° C. (dichloroethane/ethyl acetate).

Analysis: $C_{19}H_{20}N_2OCl_2.H_2O$ requires C, 59.85; H, 5.82; N, 7.35%. Found: C, 59.94; H, 5.48; N, 7.29%.

EXAMPLE 38

1-(4-Chlorophenyl)-3-amino-1,4-dihydroisoquinoline hydrochloride hemihydrate

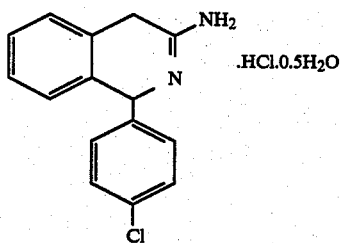

To a solution of 1-(4-chlorophenyl)-1,4-dihydroisoquinol-3-one (10.0 g, 38 mmol) in dry methylene chloride (200 ml) was added triethyloxonium tetrafluoroborate (7.8 g, 42 mmol) in one portion, under nitrogen. The mixture was stirred at room temperature for 3½ h. After cooling to −10° C., saturated potassium carbonate (aq.) (22 ml) was added with rapid stirring. After ½ h, the mixture was filtered onto dry potassium carbonate (20 g). The filtrate was refiltered, ethereal hydrogen chloride added and the solvent was removed under reduced pressure. The solid so obtained was dissolved in ethanol (200 ml) and 0.880 aq. ammonia (100 ml) was added. The solution was left at room temperature under a very slow stream of nitrogen for 3 days. The mixture was evaporated under reduced pressure (water bath temperature 30° C.) and shaken with water (200 ml), ethyl acetate (400 ml) and chloroform (200 ml). The aqueous layer was separated off and the organic layer was reextracted with water. The combined aqueous layers were evaporated under reduced pressure to give a bright yellow solid. This material was extracted with water (2×25 ml), filtered and evaporated under reduced pressure. The residue was dissolved in ethanol (20 ml) and filtered and evaporated under reduced pressure.

This gave 1-(4-chlorophenyl)-3-amino-1,4-dihydroisoquinoline hydrochloride hemihydrate (3.6 g, 32%) as a pale yellow solid. A sample was recrystallised from chloroform/ethyl acetate to give a white crystalline solid m.p. 222°-4° C.

Analysis: $C_{15}H_{14}N_2Cl_2.0.5H_2O$ requires C, 59.62; H, 5.00; N, 9.27%. Found: C, 60.00; H, 4.60; N, 9.17%.

Similarly prepared were:

EXAMPLE 39

1-(4-Chlorophenyl)-3-methylamino-1,4-dihydroisoquinoline hydrochloride hemihydrate

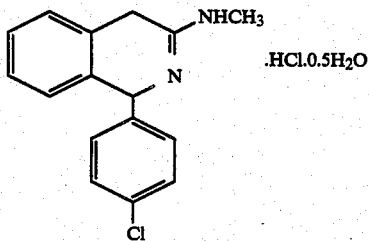

m.p. 165°-8° C. (chloroform/ether).

Analysis: $C_{16}H_{16}N_2Cl_2.0.5H_2O$ requires C, 60.77; H, 5.42; N, 8.86%. Found: C, 60.71; H, 5.40; N, 8.89%.

EXAMPLE 40

3-Amino-1-(2-fluorophenyl)-1,4-dihydroisoquinoline hydrochloride

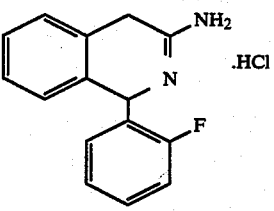

m.p. 230°-238° C. (Ethanol/ether).

EXAMPLE 41

3-Dimethylamino-1-(3-methanesulphonamidophenyl)-1,4-dihydroisoquinoline hydrochloride hydrate

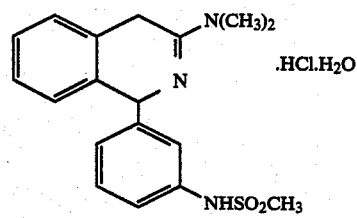

This compound was prepared from 1-(3-methanesulphonamidophenyl)-1,4-dihydroisoquinol-3-one hemihydrate in the usual manner.

m.p. 177°-180° C. (chloroform).

Analysis: $C_{18}H_{21}N_3SO_2.HCl.H_2O$ requires C, 54.35; H, 6.05; N, 10.55; Cl, 8.9%. Found: C, 54.55; H, 5.9; N, 10.5; Cl, 8.85%.

EXAMPLE 42

1-(4-Carboxamidophenyl)-1,4-dihydro-3-dimethylaminoisoquinoline hydrochloride hemihydrate

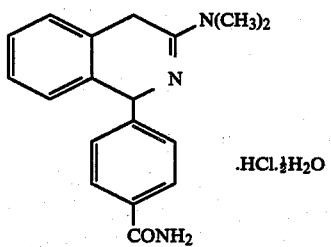

A solution of 1-(4-cyanophenyl)-1,4-dihydro-3-dimethylaminoisoquinoline hydrochloride (1.30 g, 4.2 mmol) in concentrated hydrochloric acid (6 ml) was heated at 90° C. for 90 min. The solution was cooled and diluted with water, then washed with ethyl acetate. After basification with 40% sodium hydroxide solution, the aqueous suspension was extracted with ethyl acetate and the aqueous solution was retained. The extracts were washed with brine, dried (MgSO₄), treated with ethereal hydrogen chloride and evaporated to leave the title compound as a pale yellow solid (490 mg, 36%). Recrystallisation from ethanol/ethyl acetate gave crystals, m.p. 243°-248° C.

Analysis: Found C, 64.11; H, 6.22; N, 12.31; Cl, 10.33%. $C_{18}H_{20}N_3OCl.\frac{1}{2}H_2O$ requires C, 63.80; H, 6.24; N, 12.40; Cl, 10.46%.

IR νmax (Nujol) 1670 cm$^{-1}$.

EXAMPLE 43

1-(4-Carbomethoxyphenyl)-1,4-dihydro-3-dimethylaminoisoquinoline hydrochloride

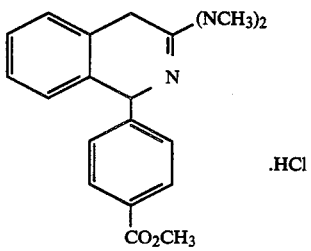

The basic aqueous solution from the above experiment was made acidic with 5N hydrochloric acid, and evaporated to dryness to leave a white solid, containing 1-(4-carboxyphenyl)-1,4-dihydro-3-dimethylaminoisoquinoline hydrochloride. The crude acid was suspended in methanol (100 ml) and ethereal hydrogen chloride (2 ml) at room temperature for 16 h. The suspension was filtered and the filtrate was evaporated under reduced pressure. The residue was dissolved in dilute hydrochloric acid, washed with ethyl acetate, then basified with 10% sodium hydroxide solution and extracted with ethyl acetate. The extracts were washed with brine, dried (MgSO$_4$) and ethereal HCl was added. The solvent was removed under reduced pressure and the residual solid was recrystallised from dichloroethane/ethyl acetate to give 1-(4-carbomethoxyphenyl)-1,4-dihydro-3-dimethylamino-isoquinoline hydrochloride as a pale yellow powder, m.p. 187°–193° C.

EXAMPLE 44

1-(2-Chloro-6-fluorophenyl)-3-dimethylamino-6-methoxy-1,4-dihydroisoquinoline hydrochloride

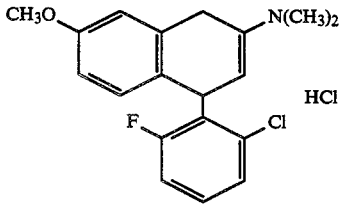

m.p. 219°–222° C. (dichloromethane/toluene).

EXAMPLE 45

1-(2-Chloro-6-fluorophenyl)-3-dimethylamino-8-methoxy-1,4-dihydroisoquinoline hydrochloride hydrate

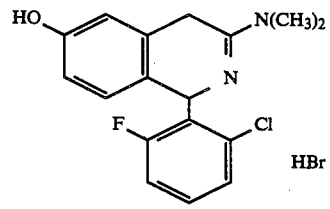

m.p. 281°–284° C. (methanol/ethanol/ethyl acetate)

Analysis: $C_{18}H_{19}N_2OCl_2F.H_2O$ requires C, 55.82; H, 5.47; N, 7.23%. Found: C, 56.14; H, 5.17; N, 7.20%.

EXAMPLE 46

1-(2-Chloro-6-fluorophenyl)-3-dimethylamino-6-hydroxy-1,4-dihydroisoquinoline hydrobromide

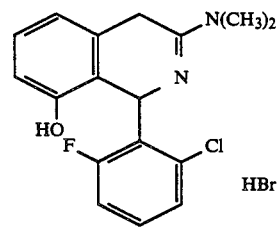

m.p. 297°–300° C. (methanol/ethyl acetate).

Analysis: $C_{17}H_{17}N_2OCl_2BrF$ requires C, 51.09; H, 4.29; N, 7.01%. Found: C, 50.86; H, 4.4; N, 6.89%.

EXAMPLE 47

1-(2-Chloro-6-fluorophenyl)-3-dimethylamino-8-hydroxy-1,4-dihydroisoquinoline hydrobromide m.p. >330° C. (CH$_3$OH/EtOAc).

EXAMPLES 48 TO 57

The following examples are prepared analogously.

1-(2-Cyanophenyl)-3-dimethylamino-1,4-dihydroisoquinoline hydrochloride

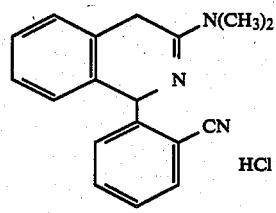 (48)

1-(2-Chlorophenyl)-3-dimethylamino-6-thiomethyl-1,4-dihydroisoquinoline hydrochloride

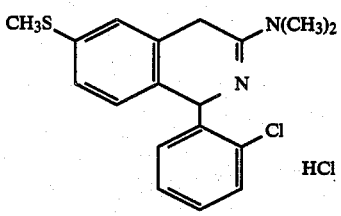 (49)

1-(2-Chlorophenyl)-7-ethyl-3-dimethylamino-1,4-dihydroisoquinoline hydrochloride

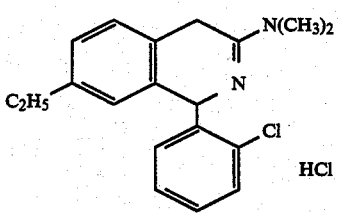 (50)

1-(2-Chlorophenyl)-6-ethyl-3-dimethylamino-1,4-dihydroisoquinoline hydrochloride

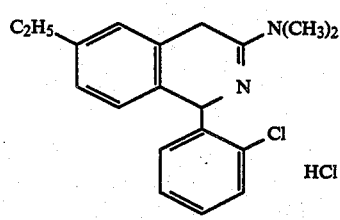 (51)

1-(2-Chlorophenyl)-3-dimethylamino-5-methoxy-1,4-dihydroisoquinoline hydrochloride

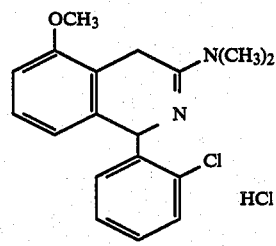 (52)

1-(2-Chlorophenyl)-3-dimethylamino-7-methoxy-1,4-dihydroisoquinoline hydrochloride

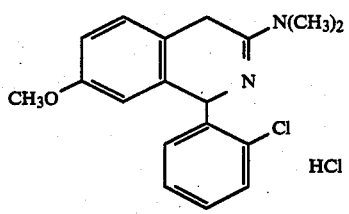 (53)

1-(2-Chlorophenyl)-3-dimethylamino-5-hydroxy-1,4-dihydroisoquinoline hydrobromide

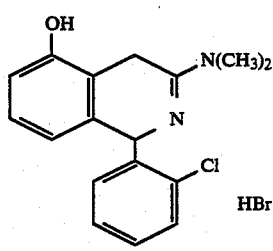 (54)

1-(2-Chlorophenyl)-3-dimethylamino-7-hydroxy-1,4-dihydroisoquinoline hydrobromide

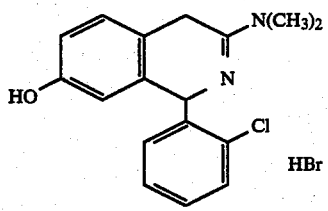 (55)

1-(2-Chlorophenyl)-7-chloro-3-dimethylamino-6-methoxy-1,4-dihydroisoquinoline hydrochloride

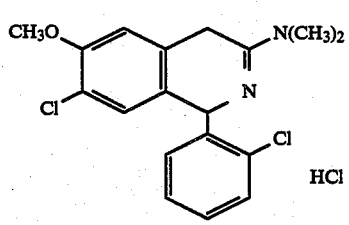 (56)

1-(2-Chlorophenyl)-3-dimethylamino-4,6,7,8-tetrahydro-1H-cyclopent[g]isoquinoline hydrochloride

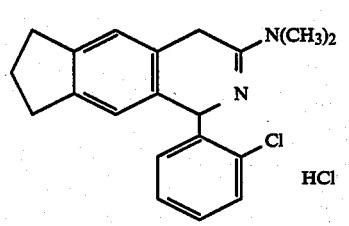 (57)

Pharmacological Data

(i) ADJUVANT ARTHRITIS TEST IN THE RAT

The test is as described by Newbould, Brit. J. Pharmacol., 1963, 21, 127–136. Compounds were active at the doses shown below.

| COMPOUND OF EXAMPLE | ACTIVE DOSE mg/kg |
|---|---|
| 1 | 25 (p.o.) |
| 2 | 12.5 (p.o.) |
| 10 | 25 (p.o.) |
| 30 | 12.5 (i.p.) |
| 31 | 20 (i.p.) |
| 32 | 25 (i.p.) |

(ii) CARRAGEENIN-INDUCED PLEURISY IN THE RAT

This model of monocyte accumulation is based on the method of R. Vinegar, J. F. Truax, J. L. Selph and F. A. Voelker [Federation Proceedings 41, 2588–2595, 1982].

0.2 ml of a 2.0% solution of -carrageenin (Viscarin 402) in saline was injected intrapleurally in anaesthetised rats (wt. approx. 175–200 g). Compounds were administered 1 hour before carrageenin and at 24 and 48 hours after carrageenin. 72 hours later 4.0 ml of EDTA solution (5 g EDTA in 100 ml of 0.9% saline and 325 mg phenol red added together with saline to 1 liter) was injected intrapleurally after killing the animals, and the exudate removed with a syringe through the diaphragm. Exudate volume was measured spectrophotometrically (560 nm) and cellular content estimated with a DNA assay [Karsten U. and Wollenberger A. Anal. Biochem. 77, 464–470, 1977].

Compounds were active at the doses shown below:

| COMPOUND OF EXAMPLE | ACTIVE DOSE mg/kg |
|---|---|
| 1 | 3 (p.o.) |
| 2 | 12.5 (p.o.) |
| 4 | 12.5 (p.o.) |
| 8 | 0.11 (p.o.) |

(iii) Inhibition of 5-lipoxygenase Activity

5-Lipoxygenase enzyme was prepared as a 10,000 g supernatant from RBL-1 cells by the method of Jakschik [Jakschik, B. A., F. F. Sun, L. M. Lee, and M. M. Steinhoff, 1980, Biochem. Biophys. Res. Comm. 95, 103]. The 10,000 g supernatant was diluted with homogenization buffer to the equivalent of $1.5-2.5 \times 10^7$ cells. $ml^{-1}$ and made 2 mM with respect to $CaCl_2$. Aliquots of 0.5 ml were then dispensed into tubes, and incubated at 29° C. with 5 μl ethanol or compound in ethanol at the desired concentration for 2 min. Then [1-$^{14}$C] arachidonic acid was added in buffer to give a final concentration of 6.3 μm and 0.2 μCi per incubation, and the reaction continued at 29° C. for 2 min. The reaction was terminated by adding 1 ml of acetone and cooling on ice, 0.5 ml of ice-cold saline and 10 μl of 2N formic acid were added, and the mixture was extracted with $2 \times 2$ ml of chloroform. The extract was stored under $N_2$ at $-20°$ C. until analysis by chromatography. Activity was measured as the percentage of total radioactivity found in 5-HETE and 5,12-diHETE, and inhibition calculated as the decrease in formation of the sum of these two species in compound-treated incubates relative to control incubates. At concentration of 5 μm, the compounds of Examples 1 and 30 gave an inhibition of 15% (p<0.05) and 37% (p<0.05) respectively. At a concentration of 50 μm the compounds of Examples 1 and 30 gave an inhibition of 50% (p<0.05) and 92% (p<0.5) respectively.

(P values as assessed by the students 't' test).

Toxicity

No toxic effects were observed in the above tests.

We claim:

1. A compound of formula (I) or a pharmaceutically acceptable salt or solvate thereof:

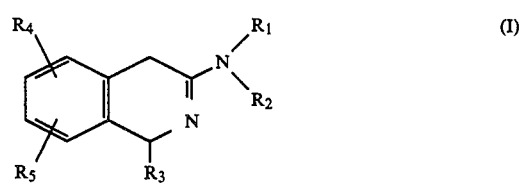

wherein:
$R_1$ and $R_2$ are independently hydrogen, $C_{1-6}$ alkyl or together are a group X which is $C_{3-6}$ polymethylene in which one carbon atom in optionally replaced by an oxygen or sulphur atom or by $NR_6$ is hydrogen or $C_{1-6}$ alkyl; $R_3$ is phenyl, optionally substituted by one or more substituents selected from halogen, $CF_3$, nitro, $C_{1-6}$ alkoxy, $C_{1-6}$ alkylthio, $C_{2-7}$ alkanoyl, carboxyl, $C_{1-6}$ alkoxycarbonyl, cyano, $CONR_7R_8$ wherein $R_7$ and $R_8$ are selected from hydrogen or $C_{1-6}$ alkyl or together are a group X; $NR_9R_{10}$ wherein $R_9$ and $R_{10}$ are selected from hydrogen, $C_{1-6}$ alkyl, $C_{2-7}$ alkanoyl or $C_{1-6}$ alkylsulphonyl or together are a group X; $SO_2NR_{11}R_{12}$ wherein $R_{11}$ and $R_{12}$ are selected from hydrogen or $C_{1-6}$ alkyl or together are a group X, or $S(O)_mR_{13}$ wherein m is 1 or 2 and $R_{13}$ is $C_{1-6}$ alkyl;

$R_4$ and $R_5$ are independently selected from hydrogen, $C_{1-6}$ alkyl, cyano, amino, aminocarbonyl or aminocarbamoyl optional substituted by one or two $C_{1-6}$ alkyl groups or together a group X, halogen, $CF_3$, nitro, $C_{1-6}$ alkoxy, $C_{1-6}$, alkylthio, $C_{2-7}$ alkanoyloxy, $C_{1-6}$ alkoxy or hydroxy, or together are methylenedioxy or $C_{3-5}$ polymethylene.

2. A compound according to claim 1 of formula (II):

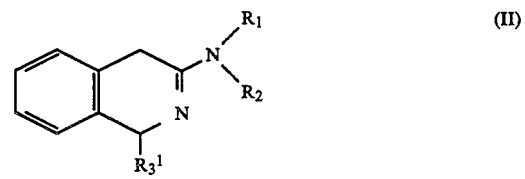

wherein $R_3^1$ is phenyl optionally substituted by one or two of halo, nitro, cyano or methyl; and the remaining variables are as defined in claim 1.

3. A compound according to claim 1 of formula (III):

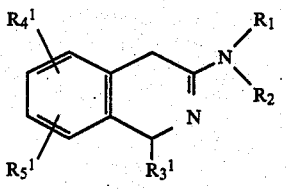

(III)

wherein R$_4^1$ is hydrogen, halogen, C$_{1-6}$ alkoxy, C$_{2-7}$ alkanoyloxy or hydroxy and R$_5^1$ is C$_{1-6}$ alkoxy, C$_{2-7}$ alkanoyloxy or hydroxy; or R$_4^1$ and R$_5^1$ together are methylenedioxy; and R$_3^1$ is as defined in claim 2.

4. A compound according to claim 3 of formula (IV):

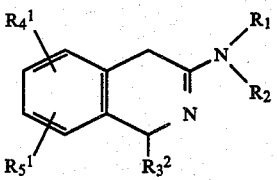

(IV)

wherein R$_3^2$ is phenyl substituted by one or two of fluoro, chloro or bromo or cyano and the remaining variables are as defined in claim 3.

5. A compound according to claim 4 wherein R$_4^1$ is 6-hydroxy or 6-methoxy and R$_5$ is hydrogen; R$_4^1$ is hydrogen and R$_5^1$ is 8-hydroxy or 8-methoxy or R$^4{}_1$ and R$^5{}_1$ are 6, 7-dihydroxy.

6. A compound according to any one of claims 1 wherein R$_1$ is hydrogen or methyl and R$_2$ is methyl.

7. A compound according to any one of claims 1 wherein R$_3$, R$_3^1$ or R$_3^2$ is 2-chlorophenyl, 2-chloro-6-fluorophenyl or 6-chloro-6-fluorophenyl.

8.

1-(2-Chlorophenyl)-3-dimethylamino-1,4-dihydroisoquinoline,
1-(4-chlorophenyl)-3-dimethylamino-1,4-dihydroisoquinoline,
1-(4-nitrophenyl)-3-dimethylamino-1,4-dihydroisoquinoline,
1-(2-bromophenyl)-3-dimethylamino-1,4-dihydroisoquinoline,
1-(2-trifluoromethylphenyl)-3-dimethylamino-1,4-dihydroisoquinoline,
1-(2,4-dichlorophenyl)-3-dimethylamino-1,4-dihydroisoquinoline,
1-(2,6-dichlorophenyl)-3-dimethylamino-1,4-dihydroisoquinoline,
1-(2-chloro-6-fluorophenyl)-3-dimethylamino-1,4-dihydroisoquinoline,
1-(3-chlorophenyl)-3-dimethylamino-1,4-dihydroisoquinoline,
1-(2-fluorophenyl)-1,4-dihydro-3-dimethylaminoisoquinoline,
1-(4-bromophenyl)-1,4-dihydro-3-dimethylaminoisoquinoline,
1-(2-chloro-6-methylphenyl)-3-dimethylamino-1,4-dihydroisoquinoline,
1-(2-chloro-3-methylphenyl)-3-dimethylamino-1,4-dihydroisoquinoline,
1-(3-methoxy-4-chlorophenyl)-3-dimethylamino-1,4-dihydroisoquinoline,
1-(2-methanesulphonylphenyl)-3-dimethylamino-1,4-dihydroisoquinoline,
1-(4-methanesulphonylphenyl)-3-dimethylamino-1,4-dihydroisoquinoline,
1-(4-cyanophenyl)-1,4-dihydro-3-dimethylaminoisoquinoline,
1-(4-chlorophenyl)-3-dimethylamino-7-methyl-1,4-dihydroisoquinoline,
3-dimethylamino-1-phenyl-1,4-dihydroisoquinoline,
7-chloro-1-(4-chlorophenyl)-3-dimethylamino-1,4-dihydroisoquinoline,
1-(4-chlorophenyl)-3-dimethylamino-7-fluoro-1,4-dihydroisoquinoline,
1-(4-chlorophenyl)-3-dimethylamino-6-fluoro-1,4-dihydroisoquinoline,
1-(4-chlorophenyl)-3-dimethylamino-6,7-dimethoxy-1,4-dihydroisoquinoline,
1-(4-chlorophenyl)-3-dimethylamino-8-methoxy-1,4-dihydroisoquinoline,
1-(4-chlorophenyl)-3-dimethylamino-6-methoxy-1,4-dihyroisoquinoline,
1-(2-cyanophenyl)-3-dimethylamino-1,4-dihydroisoquinoline,
1-(2-chlorophenyl)-3-dimethylamino-6-thiomethyl-1,4-dihydroisoquinoline,
1-(2-chlorophenyl)-7-ethyl-3-dimethylamino-1,4-dihydroisoquinoline,
1-(2-chlorophenyl)-6-ethyl-3-dimethylamino-1,4-dihydroisoquinoline,
1-(2-chlorophenyl)-3-dimethylamino-5-methoxy-1,4-dihydroisoquinoline,
1-(2-chlorophenyl)-3-dimethylamino-7-methoxy-1,4-dihydroisoquinoline,
1-(2-chlorophenyl)-3-dimethylamino-5-hydroxy-1,4-dihydroisoquinoline,
1-(2-chlorophenyl)-3-dimethylamino-7-hydroxy-1,4-dihydroisoquinoline,
1-(2-chlorophenyl)-7-chloro-3-dimethylamino-6-methoxy-1,4-dihydroisoquinoline or
1-(2-chlorophenyl)-3-dimethylamino-4,6,7,8 tetrahydro-1H-cyclopent[g]isoquinoline,
or a pharmaceutically acceptable salt of any of the foregoing.

9.

1-(2-Chlorophenyl)-3-dimethylamino-6-methoxy-1,4-dihydroisoquinoline,
1-(2-chlorophenyl)-3-dimethylamino-8-methoxy-1,4-dihydroisoquinoline,
1-(2-chlorophenyl)-3-dimethylamino-6-hydroxy-1,4-dihydroisoquinoline,
1-(2-chlorophenyl)-3-dimethylamino-8-hydroxy-1,4-dihydroisoquinoline,
1-(2-chloro-6-fluorophenyl)-3-dimethylamino-6-methoxy-1,4-dihydroisoquinoline,
1-(2-chloro-6-fluorophenyl)-3-dimethylamino-8-methoxy-1,4-dihydroisoquinoline,
1-(2-chloro-6-fluorophenyl)-3-dimethylamino-6-hydroxy-1,4-dihydroisoquinoline,
1-(2-chloro-6-fluorophenyl)-3-dimethylamino-8-hydroxy-1,4-dihydroisoquinoline,
or a pharmaceutically acceptable salt of any of the foregoing.

10. A process for the preparation of a compound according to any one of claims 1, or a pharmaceutically acceptable salt thereof which process comprises the reaction of a compound of formula (V):

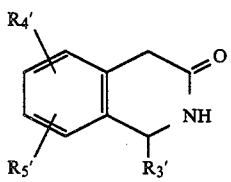 (V)

wherein $R_3'$, $R_4'$ and $R_5'$ are $R_3$, $R_4$ and $R_5$ or groups or atoms convertible thereto; with either (i) $R_1'R_2'NCOQ_1$ wherein $Q_1$ is a leaving group or
(ii) an alkylating agent followed by treatment with $R_1'R_2'NH$ wherein $R_1'$ and $R_2'$ are $R_1$ and $R_2$ or groups or atoms convertible thereto;

and thereafter optionally converting $R_1'$ and/or $R_2'$ when other than $R_1$ and/or $R_2$ to $R_1$ and/or $R_2$ respectively; converting $R_3'$, $R_4'$ or $R_5'$ to $R_3$, $R_4$ and/or $R_5$ respectively; and/or forming a pharmaceutically acceptable salt thereof.

11. A pharmaceutical composition, useful in the treatment of inflammatory and/or painful conditions, including rheumatism, in mammals, which comprises a pharmaceutically effective amount of a compound according to any one of claims 1 to 9 or a pharmaceutically acceptable salt or solvate thereof and a pharmaceutically acceptable carrier.

12. A method of treating inflammatory and/or painful conditions, including rheumatism, in mammals, which comprises administering to a mammal a pharmaceutically effective amount of a compound according to any one of claims 1 to 9 or a pharmaceutically acceptable salt or solvate thereof.

* * * * *